United States Patent [19]

Snyder

[11] 4,204,952
[45] May 27, 1980

[54] CHROMATOGRAPHIC APPARATUS AND METHOD

[75] Inventor: Lloyd R. Snyder, Yorktown Heights, N.Y.

[73] Assignee: Technicon Instruments Corporation, Tarrytown, N.Y.

[21] Appl. No.: 922,712

[22] Filed: Jul. 7, 1978

[51] Int. Cl.² .................................................. B01D 15/08
[52] U.S. Cl. ........................................ 210/31 C; 55/67
[58] Field of Search ............. 210/31 C, 198 C; 55/67, 55/386, 197

[56] References Cited

U.S. PATENT DOCUMENTS

| | | | |
|---|---|---|---|
| 3,002,583 | 10/1961 | Findlay | 55/67 |
| 3,373,872 | 3/1968 | Hrdina | 210/198 C |
| 3,508,880 | 4/1970 | Hrdina | 210/198 C |
| 3,897,213 | 7/1975 | Stevens | 210/31 C |
| 3,918,906 | 11/1975 | Small et al. | 210/31 C |
| 4,001,112 | 1/1977 | Barker | 210/31 C |
| 4,054,430 | 10/1977 | Valentin et al. | 55/67 |
| 4,070,284 | 1/1978 | Fudita et al. | 210/198 C |

OTHER PUBLICATIONS

"Two Stage Liquid Chromatograph" by Simmons et al. in Analytical Chemistry, vol. 30, p. 32, 1/1958.
"Gas Chromatography" by Schupp in Technique of Organic Chemistry, vol. XIII, p. 241, 1968.
"Continuous Chromatographic Refining Using a New Compact Chromatographic Machine", by Barker et al. in Journal of Chromatography Science, vol. 7, p. 246, 7/1969.
"Comparisons of Normal Elutions, Coupled Columns, and Solvent Flow or Temperature Programming in Liquid Chromatography" by Snyder in Journal of Chromatography Science, vol. 8, p. 692, 12/1970.

*Primary Examiner*—John Adee
*Attorney, Agent, or Firm*—S. P. Tedesco

[57] ABSTRACT

An apparatus and method for increasing the throughput of a chromatographic system by passing several samples in seriatim through tandemly connected first and second chromatographic columns. The eluant from the first column is sampled, or fractionated, and fractions of each of the samples are passed through the second column for further separation. A switching of the sampling valve, disposed between the first and second columns, effects such fractioning. The pumping rate for the second column may be different from that of the first column and allows that two or more sample fractions can occupy the second column concurrently.

5 Claims, 7 Drawing Figures

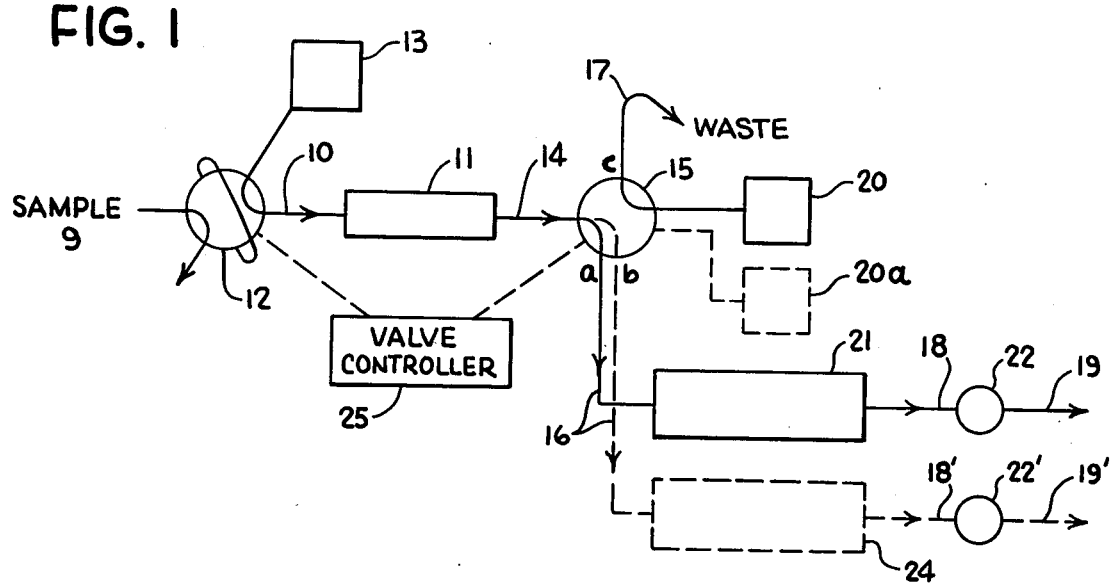
FIG. 1
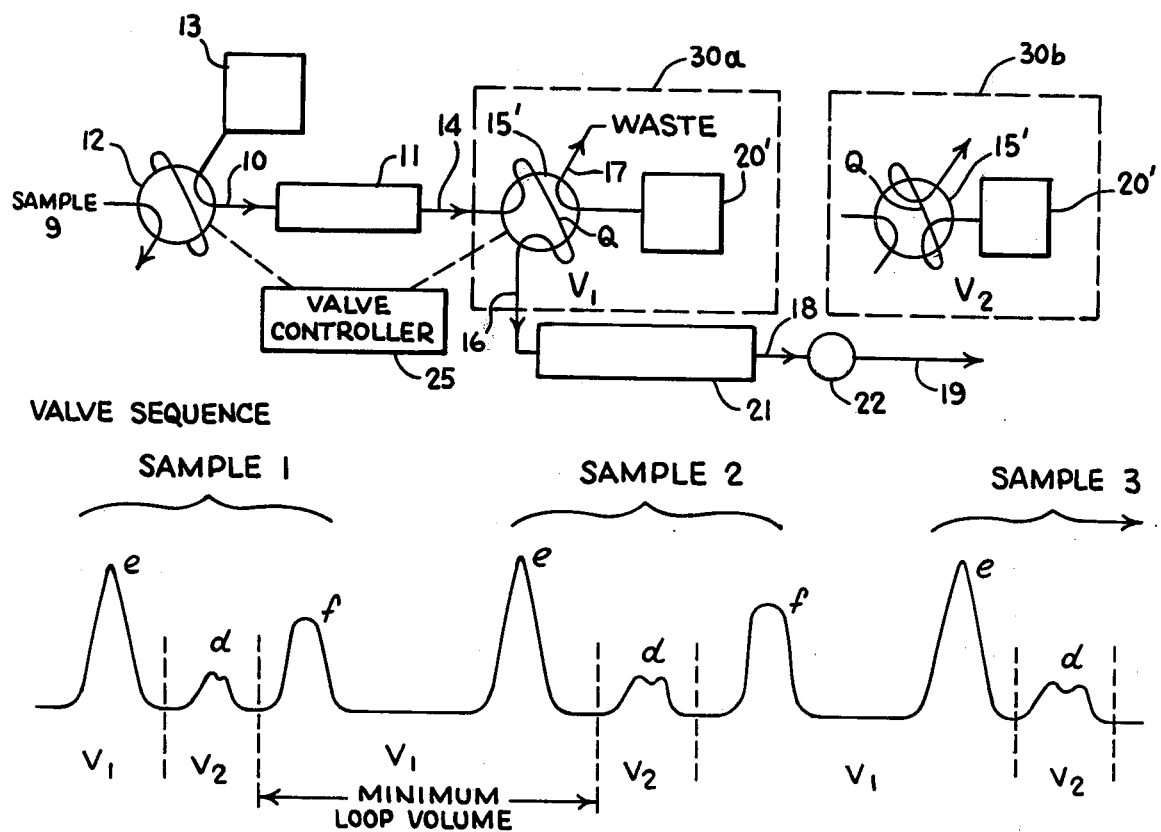
FIG. 3
FIG. 4

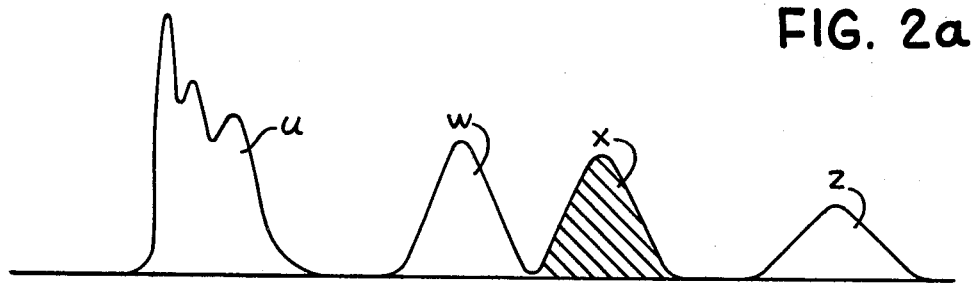
FIG. 2a
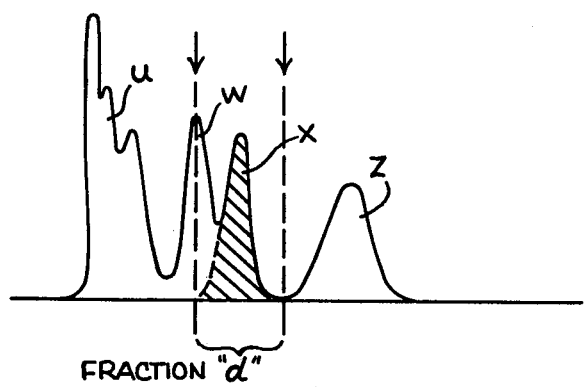
FIG. 2b
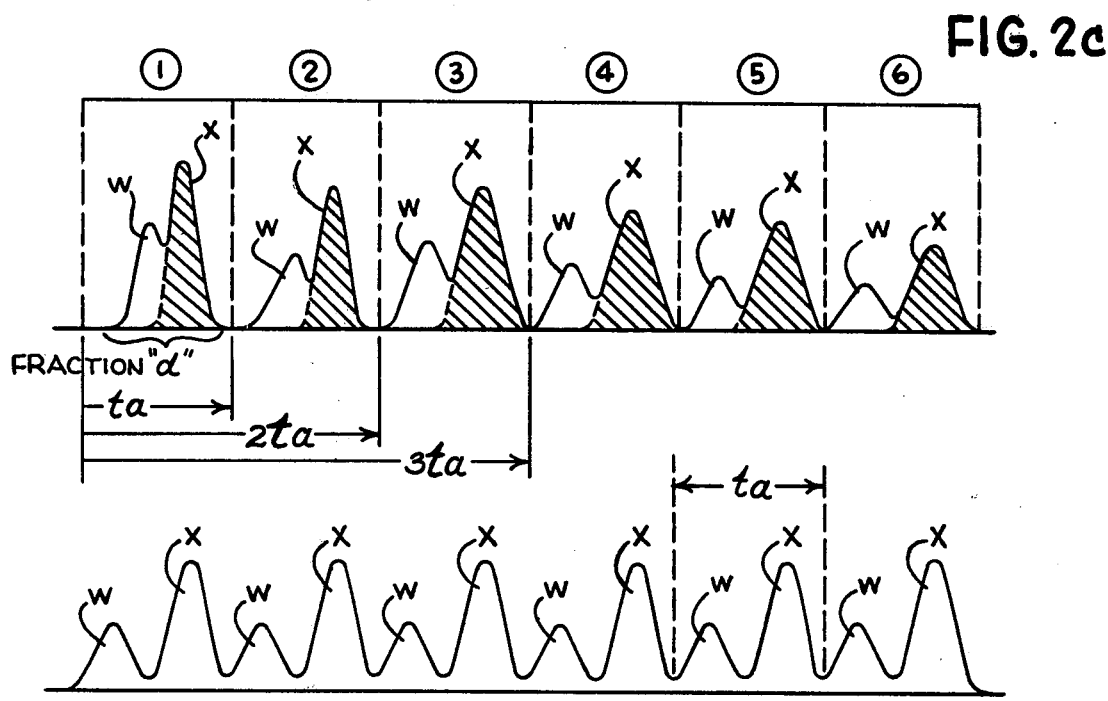
FIG. 2c
FIG. 2d

CHROMATOGRAPHIC APPARATUS AND METHOD

FIELD OF THE INVENTION

The present invention relates to chromatographic apparatus and method, both liquid and gas, having an improved throughput, or processing rate.

BACKGROUND OF THE INVENTION

In chromatographic systems of the prior art, a single sample to be separated wastefully occupied only a small portion of a chromatographic column. A second sample was not introduced into such column until the first sample had been completely eluted. Accordingly, chromatographic separation of samples was an inefficient and time-consuming procedure. The present invention contemplates a much more efficient use of a chromatographic column. This increased efficiency is achieved by initially separating each of a number of samples fed seriatim into a first column into its individual components on a coarse basis. The eluant passing from the first column is sampled, so as to pass particular fractions of each sample seriatim through a second column, wherein a complete separation of the constituents is effected. This technique provides a passage of many sample fractions through the system concurrently. The over-all result is a dramatic increase in the throughput of the chromatographic system.

PRIOR ART

The art of chromatography is highly prolific and varied in its procedures and apparatuses for purifying and analyzing samples. Some prior systems used multiple stages to separate complex samples exhibiting a difficulty towards separation. Such systems used two or more columns arranged in series and packed with different column packings. Description of such systems can be found in the articles to: "TWO-STAGE GAS-LIQUID CHROMATOGRAPHY", M.C. Simmons and L.R. Snyder, *Analytical Chemistry*, Vol. 30, page 32, January, 1958, and "GAS CHROMATOGRAPHY," Orion Edwin Schupp III, *Technique of Organic Chemistry*, Vol. XIII, page 251, 1968. These prior art systems feature a switching valve between the two columns to select one or more adjacent bands for preseparation by a short column and further separation by a long column, not unlike the inventive system. However, these systems do not provide an increase in throughout. It is characteristic of such systems that only one sample is passing through the system at any one time. The principle of operation of these prior art systems is differing separation selectivity in each column.

The Schupp article discusses special problems with dilute samples, wherein a pre-column is used followed by a switching valve serially connecting a second column which may be packed with the same material. Low-boiling components of the sample are allowed to vent to waste in the first column. The temperature of the pre-column is raised to effect faster elution of sample components of interest, and a normal separation of the residual sample results. The object of this technique is to vent large volumes of solvent or other low-boiling compounds of no interest to waste prior to initiation of the main separation. This method eliminates the adverse effects produced by these materials upon column separation. High-boilers, which require a long elution time, are held on the first column until separation is completed. They are removed from the first column by means of back-flushing or other well-known techniques.

Another multiple column system is illustrated in the reference to "COMPARISONS OF NORMAL ELUTION, COUPLED-COLUMNS, AND SOLVENT, FLOW OR TEMPERATURE PROGRAMMING IN LIQUID CHROMATOGRAPHY", L.R. Snyder, *Journal of Chromatographic Science*, Vol. 8, page 692, December, 1970. Such system is particularly useful for difficult-to-analyze samples containing many constituents. Two or more columns are connected in parallel and/or series and have different retention strengths. Such system is adapted to divert unretained sample components that elute early from the weak-retention-strength column to the strong-retention-strength column. This will provide resolution of weakly-retained components. This procedure is similar in effect to such other procedures as gradient elution, temperature programming and flow programming.

In such system, only one sample is in the system at any given time. Accordingly, the throughput of this system is not particularly high.

Another technique features a continuous chromatographic refining of a sample. Continuous separation of a single sample is done for the purposes of preparing large quantities of pure material. Such a method is shown in the reference to "CONTINUOUS CHROMATOGRAPHIC REFINING USING A NEW COMPACT CHROMATOGRAPHIC MACHINE", P.E. Barker and S. Al-Madfai, *Journal of Chromatographic Science*, Vol. 7, page 426, July,1969; R.A. Findlay, U.S. Pat. No. 3,002,583, issued Oct. 3, 1961; and Barker et al U.S. Pat. No. 4,001,112, issued Jan. 4, 1977. These latter three references teach a refining or purifying of a constituent by chromatographic procedures, and are not concerned with increasing the throughput of the system. Discrete samples are not introduced successively or travel concurrently through a separatory column.

The patents to J. Hrdina, U.S. Pat. Nos. 3,373,872, issued Mar. 19, 1968 and 3,508,880, issued Apr. 28, 1970, depict chromatographic systems having more than one column operated by a single pump. These patents, like the previous references, do not relate to passing a multiplicity of discrete samples through a column or system at any one given time.

SUMMARY OF THE INVENTION

As aforementioned, the present invention seeks a dramatic increase in the throughput of a liquid or gas chromatographic system. First and second columns are arranged in tandem and may be packed with the same or different material. A switching, or sampling, valve is located between the columns to fractionate each sample eluant passing seriatim from the first column. The fractional eluant may contain several adjacent bands of compounds which are fed to the second column for a more complete separation. Unwanted eluants are discarded to waste by the switching valve as they precede or follow the bands of interest. In other words, the switching valve takes a cut or fraction from each sample passing from the first column and feeds such fraction to the second column.

As the second column is fed only a small fraction of the sample, one or more fractions of different samples can be passed therethrough concurrently and separation is more efficiently effected.

A subsequent sample of similar constituents is now fed through the first column as remaining material from the prior sample leaves the first column. The second and subsequent samples are fractoned similarly to the first sample. This process will feed the discrete sample fractions into the second column at a controlled rate. When the first sample fraction has moved a discrete distance along the second column, a subsequent sample fraction is passed to the second column, such that a string of adjacent sample fractions is moved along the second column concurrently. This dramatically improves the throughput of the chromatographic system.

The injection rate and volume of different sample fractions fed to the second column are controlled in respect of the rate of flow through the second column. Accordingly, the constituent of interest in each sample fraction will be separated but will not overlap with other adjacent constituents when eluted from the second column. Furthermore, the introduction of samples into the first column may be synchronized with the introduction of sample fractions into the second column. Thus, a continuous process of analyzing discrete adjacent samples is achieved wherein discrete non-overlapping constituents of interest contained in the eluants of each sample fraction are obtained.

OBJECTS OF THE INVENTION

The greatest consequence of this continuity is that, with just a few minor changes in apparatus, a new system having a dramatic increase in throughput is created.

It is an object of this invention to provide an improved chromatographic method and apparatus;

It is another object of the invention to provide a chromatographic system having an improved throughput; and It is a further object of this invention to provide a continuously fed chromatographic system wherein a plurality of discrete fractions of samples are passing through a chromatographic column of the system concurrently.

BRIEF DESCRIPTION OF THE DRAWINGS

These and other objects of the invention will be better understood and will become more apparent with reference to the accompanying drawings, in which:

FIG. 1 is a schematic diagram of the chromatographic system of this invention;

FIGS. 2a-2d are various schematic diagrams of compounds travelling along separately columns. FIG. 2a shows the separation of compounds within a sufficiently long column equal in length to the short and long columns of FIG. 1, such that closely-eluting compounds "W" and "X" are completely separated;

FIG. 2b depicts travel of compounds within the short column as shown in FIG. 1, such that closely-eluting compounds "W" and "X" are overlapping each other;

FIG. 2c illustrates a plurality of fractions or cuts ("d") taken from the short column (see FIG. 2b) which have been introduced to, and are passing through, the long column shown in FIG. 1;

FIG. 2d shows the successive elution of compounds "W" and "X" of adjacent sample fractions emerging from the long column of FIG. 1 in accordance with the invention;

FIG. 3 depicts a schematic diagram of an alternate embodiment to the chromatographic system of FIG. 1; and FIG. 4 illustrates a schematic diagram of the valve sequence for the embodiment shown in FIG. 3.

DETAILED DESCRIPTION

The present invention contemplates the passage of a series of samples through a first chromatographic column for crudely separating the constituents thereof. A fraction of each sample eluant passing from the first column is directed to a second column, which completes the separation. Passage of such fractions through the second column is effected at a controlled rate, to ensure that the particular consituents of interest in each fraction do not overlap (or otherwise are sufficiently separated) when eluted from the second column. The throughput of the system is substantially increased, by passing a plurality of fractions of different samples through the second column concurrently.

The apparatus of the invention features: a first chromatographic column; means to pass a series of samples into the first column; a second chromatographic column; and means to pass the fractions of each sample eluant from the first column into the second column at a controlled rate to ensure that constituents of interest of each sample fraction eluting from the second column will be sufficiently separated for purposes of analysis.

Now referring to FIG. 1, a sample 9 is introduced, as indicated by arrow 10, along with a solvent into a first chromatographic column 11 by means of an injection valve 12 and a continuously pumping of high pressure pump 13. The sample usually contains several compounds, one or more of which are particular constituents of interest to be ultimately separated from the other compounds and analyzed. The sample 9 passes through column 11, under the impetus of pump 13, and the eluent passing from column 11, as indicated by arrow 14 is fed to a switching or sampling valve 15. The purpose of valve 15 is to allow a cut of the sample or otherwise separate a fraction containing the particular constituent of interest from other compounds in the sample. The switching valve 15 feeds such constituent under the impetus of high pressure pump 13, as indicated by arrow 16, from outlet a to a second chromatographic column 21. The fraction obtained by valve 15 is a crude cut of sample 9 that contains the constituent of interest, along with other closely-eluting compounds, which are not completely separated. Accordingly, a further separation by column 21 is required. Continuously operating high pressure pump 20 supplies the impetus for driving each separated fraction through column 21 during further elution of column 11 by pump 13. Other portions of the eluant leaving column 11 which are not associated with the constituent of interest, are discarded from the system from outlet c of valve 15, as indicated by arrow 17. If desired, however, such portions may be further fractionated and passed to a third column 24 (shown in phantom) for separation and analysis of an additional constituent. Additional column 24 is connected to a second outlet b of valve 15, the outlet being connected to column 24 as shown. The fraction delivered from outlet b of vavle 15 is fed onto column 24 under the impetus of pump 13, and subsequently driven through column 24 by high pressure pump 20a.

The fraction of the original sample 9 exiting column 21 and/or column 24 is fed (as indicated by arrows 18 and 18') to detectors 22 and 22', respectively. The eluant is then discarded, as indicated by arrows 19 and 19', respectively.

The detectors 22 and 22', respectively, may be photometers or spectrophotometers. Alternately, they can be refractometers, electrochemical detectors, fluorometers, or conductivity detectors, etc. The purpose of such detectors is to quantify, or otherwise measure the amount of the particular constituent of interest in the eluant passing the associated column.

The operation of the system will be described with respect to only column 21. However, such description will be operable in respect of additional columns, such as 24, included in the system. The structure of the system associated with column 21 bears close resemblance to many prior art systems. However, pumps 13 and 20, together with valve 15, have an essentially different operation and function than do their prior art counterparts. Pumps 13 and 20 operate to introduce their respective materials into columns 11 and 21, respectively, serially, and at rates which are synchronized and controlled to provide two important features: (1) a plurality of fractions are concurrently passed through column 21, and (2) the constituent of interest in each sample fraction eluted from column 21 is substantially completely separated and does not overlap with other concurrent constituents.

To more fully understand the invention, reference is made to FIGS. 2a through 2d. FIG. 2a illustrates a complete separation of several constituents, "U", "W", "X" and "Z" in a sample. These constituents have been passed through a conventional chromatographic column having a length equal to the summed lengths of columns 11 and 21. "X" is designated (by hatching) as the particular constituent of interest to be analyzed.

If the system of FIG. 1 were operated using only column 11, the separation shown in FIG. 2b would result. As shown in FIG. 2b, the constituent of interest "X" is eluted with closely-eluting, overlapping constituent "W". Valve 15 of FIG. 1 selects the fraction designated "d", containing constituent "X" and an overlapping portion of "". This selection fraction is retained in the system, and all other portions of the sample eluant are shunted to waste, as indicated by arrow 17, from outlet c. The fraction "d" should be sufficient to ensure that essentially all of the constituent "X" is passed to column 21. As aforementioned, the retained fraction "d" of each sample 9 is passed by valve 15 along outlet b to the second column 21. FIg. 2c illustrates the further separation of the fraction "d" along column 21. Fraction "d" will be seen to contain constituent "X" intermixed, or overlapping, with constituent "W". FIG. 2c illustrates in time lapse fashion, the separation of constituents "X" and "W" as the individual fraction "d" is passed through column 21. FIG. 2c can also be a representation of several fractions passing concurrently through column 21, as will be explained hereinafter.

Column 21 will be "imagined" (for purposes of description) as being divided into six separate sections or stages 1–6, as shown. The fraction "d" is introduced into column 21 at section 1 and passes through each succeeding stage until it reaches the final section 6. It will be seen from FIG. 2c, that each stage progressively separates the fraction constituents "W" and "X", such that, at the final section 6, "W" and "X" are substantially completely separated.

If only one fraction "d" of sample 9 was passed through column 21, the processing rate or dwell time through the system would be the same as if columns 11 and 21 were connected together and no fraction was taken.

While the present invention does not process an individual sample any faster than the prior art, i.e., the dwell time of each sample in the system is not reduced, the overall sample processing rate, or throughput, however, is increased. This is accomplished by passing a multiplicity of sample fractions "d" through column 21 concurrently and at a controlled rate. After a fraction "d" of a first sample has passed through column 21 for a time $t_a$, for example, fraction "d" of a second sample can be introduced into the column without interfering with the first sample fraction. This will be seen to be true, since the first fraction will now start to occupy section 2 while the second fraction is entering section 1. At the end of time "$2t_a$", the first fraction will be fully occupying section 2, while the second fraction will be fully occupying section 1. A third fraction may now be introduced to section 1. At the end of time "$3t_a$", the first fraction will be occupying section 3, the second fraction will be within section 2, and the third fraction will be occupying section 1. This procedure can be continued until all the sections of the column 21 will be filled with fractions passing therethrough.

While column 21 is not divided into actual sections, the principle of passing several fractions into the column will be observed to be valid nonetheless. For example, it will be noted, that the space occupied by fraction "d" at any instant in section 1, is less than the distance necessary to traverse section 1 in time "$t_a$". However, fraction "d" will fully occupy all the space when it reaches section 6 due to expansion of constituents "X" and "W". In other words, the rate of introduction of sequential fractions must be controlled to adjust for expansion of the constituents as they pass through the column 21. Such control of the rate will provide that each successive sample fraction will not cause interference with other adjacent sample fractions within the columns. In other words, fraction "d" derived from different samples passed individually through column 11 is introduced and passed along column 21, in spaced, non-overlapping fashion. Also, under the impetus of pump 20, such fractions move concurrently along column 21 at a same rate, and the spacing is such that constituent "X" in each sample is fully separated when passed to detector 22 for measurement.

To achieve optimum performance, sample 9 is successively introduced into column 11 at a rate synchronized with the rate at which sample fractions "d" are passed into column 21. Accordingly, there is sufficient separation of the constituent "X" in the successive fractions leaving column 21. Synchronism is achieved by a valve controller (timer) 25, which may be a microprocessor.

FIG. 2d shows the sequence of non-overlapping fractions "d" leaving column 21, when proper synchronism is achieved.

The system diagram of FIG. 1 requires two high pressure pumps 13 and 20, respectively, to achieve the above-mentioned synchronism. Another embodiment requiring only one high pressure pump is shown in FIG. 3. In this embodiment, switching valve 15 is now replaced with a new switching valve 15' having a fraction-storage loop Q. This allows pump 20 (a high pressure pump) to be replaced by a low-pressure pump 20'.

The dashed lined boxes 30a and 30b, respectively, show the different operating phases $V_1$ and $V_2$ of switching valve 15'. Also, the compositions of the eluant passing from column 11 in respect of three successive samples $S_1$, $S_2$ and $S_3$ is shown in FIG. 4. In FIG.

4, the proper phase of valve 15' in respect of the particular constituent fractions of each sample is shown.

Initially, the switching valve 15' is switched to phase $V_1$. This allows the fraction "e" (and in subsequent samples "f") to pass into the storage loop Q while the solvent from loop Q enters column 21. However, the loop is large enough that the fractions "e" and "f" entering it do not leave the loop until it has been switched to phase $V_2$. When a fraction of interest "d" elutes from column 11, the switching valve 15' is switched to position $V_2$, and simultaneously the holding loop is flushed with fresh solvent, thus sending the unwanted components (fractions "e" and "f") to waste and desired component "d" directly onto column 21. Note pump 20' is now used in a countercurrent mode to flush the loop. The switching valve 15' now returns to $V_1$ as soon as fraction "d" has been loaded into column 21, and the loop again collects unwanted material (fractions "e" and "f") until the next desired fraction "d" is eluted from column 11.

As long as the loop on switching valve 15' is large enough to hold the volume of sample eluting between the desired fractions in two successive samples (see FIG. 4) only the desired components reach column 21. The only requirement for the low pressure pump 20' is that it pump fast enough to completely flush the loop with fresh solvent during the time the switching valve 15' is in position $V_2$.

Several modifications to the above-described systems can be made within the purview and scope of this invention. For example, the invention contemplates using a first column 11, that is shorter than the second column 21. This may be modified, and both columns may be made of equal length.

While a typical set of compounds "U", "W", "X" and "Z" were elucidated in FIGS. 2a–2d, it is naturally to be understood that other sequences of compounds will work with this invention.

The packing material for both columns 11 and 21 is desirably made the same, but not necessarily identical. There may be situations where this may not be true, as may be exercised by those skilled in this art.

Additional columns such as column 24 may be added to separate other constituents from each sample, or as a means to further improve the throughput of the system. Where increased throughput is desired, the third column 24 may alternately receive fractions along with column 21. In this mode of operation, column 11 will be fed samples twice as fast as before.

Still another mode of operation could feature three tandemly arranged columns 11, 21 and 24 which make progressively finer cuts in the eluants. For this mode of operation, another switching valve will be required between columns 21 and 24, respectively.

Having thus described the invention, what is desired to be protected by Letters Patent is presented in the following appended claims.

What is claimed is:

1. A method of increasing the throughput of a chromatographic system, which system is continuously operated and fed a series of samples, each sample containing a particular constituent of interest, said method comprising the steps of:
   (a) periodically passing a series of samples at a first controlled rate into a first chromatographic column for the purpose of separating a particular constituent of interest from each of said samples;
   (b) obtaining eluant materials for each sample passing from said first chromatographic column and retaining in said chromatographic system only that fraction of each sample containing said particular constituent of interest; and
   (c) periodically passing the retained fraction of each sample into a second chromatographic column at a second controlled rate, said first rate being in substantial synchronism with said second rate such that there is sufficient separation between the particular constituent of interest of each of said fractions leaving said second column to provide an improved throughput of the chromatographic system, because a fraction of a number of samples will be concurrently passing through said second chromatographic column.

2. The method of increasing the throughput of the chromatographic system of claim 1, wherein said fractions each comprise a number of closely-migrating compounds.

3. The method of increasing the throughput of the chromatographic system of claim 1, wherein said chromatographic system is a liquid chromatographic system.

4. The method of increasing the throughput of the chromatographic system of claim 1, wherein said chromatographic system is a gas chromatographic system.

5. The method of increasing the throughput of the chromatographic system of claim 1, further comprising the step of:
   analyzing eluant fractions passing from said second chromatographic column, said analyzing being for the purpose of quantifying the amount of the particular constituents of interest in the eluant fractions.

* * * * *